United States Patent [19]

Abadie et al.

[11] Patent Number: 4,603,372
[45] Date of Patent: Jul. 29, 1986

[54] METHOD OF FABRICATING A TEMPERATURE OR HUMIDITY SENSOR OF THE THIN FILM TYPE, AND SENSORS OBTAINED THEREBY

[75] Inventors: Gabriel Abadie, Rambouillet; Bernard Loitiere, Le Pecq, both of France

[73] Assignee: Direction de la Meteorologie du Ministere des Transports, Boulogne-Billancourt Cedex, France

[21] Appl. No.: 668,149

[22] Filed: Nov. 5, 1984

[51] Int. Cl.⁴ .................. H01G 7/00; H01L 27/02
[52] U.S. Cl. .................................. 361/286; 357/51
[58] Field of Search ........... 361/286, 312, 313, 323; 357/40, 51, 54; 29/25.42

[56] References Cited

U.S. PATENT DOCUMENTS

| | | | |
|---|---|---|---|
| 3,138,747 | 6/1964 | Stewart | 357/51 X |
| 3,273,033 | 9/1966 | Rossmeisl | 357/54 X |
| 3,323,027 | 5/1967 | Braniecki | 357/54 |
| 3,359,467 | 12/1967 | Cook | 357/51 |
| 3,381,255 | 4/1968 | Youmans | 357/51 X |
| 3,615,913 | 10/1971 | Shaw | 357/54 X |
| 3,798,145 | 3/1974 | Fournier | 357/54 X |
| 3,802,268 | 4/1974 | Thoma | 361/286 X |
| 4,393,434 | 7/1983 | Imai et al. | 361/286 |

*Primary Examiner*—Donald A. Griffin
*Attorney, Agent, or Firm*—Cushman, Darby & Cushman

[57] ABSTRACT

A printed circuit type of substrate (1) has a conductive film (2) on one face which is etched to constitute a first electrode (3) shaped as a printed circuit resistance between two connection tabs (4A, 4B) and a second electrode (5) having a connection tab (6), both electrodes are covered in a film of polymer and points (12) of the second electrode (6) are bared of polymer to put it into direct contact with a porous metal film covering the polymer film which serves as a dielectric between the said porous metal film and the first electrode (3).

14 Claims, 7 Drawing Figures

METHOD OF FABRICATING A TEMPERATURE OR HUMIDITY SENSOR OF THE THIN FILM TYPE, AND SENSORS OBTAINED THEREBY

The invention relates to a method of fabricating a thin film sensor suitable for measuring the temperature or the humidity of a gaseous medium, e.g. the natural atmosphere. The invention also relates to a sensor obtained by the method, which sensor may be a two-function sensor capable of simultaneously measuring both temperature and humidity.

BACKGROUND OF THE INVENTION

Thin film sensors are already known, in particular for measuring the degree of humidity of a gaseous medium. These sensors are essentially constituted by a smooth support which is generally made of glass, on which there are deposited a first film of metal, then a polymer film, then a second film of metal which is very thin (150 Å) so as to be porous and sensitive to water vapor. The polymer acts as a dielectric in a capacitor and is made of a hydrophilic material which is thin (10 microns) in order to ensure that the sensor's response time is short, e.g. about one second.

The properties looked for in such a sensor are obtained by accurately making thin films of constant thickness. This causes both the cost and the reject rate to be high since the polymer film is often too thin and thus forms a short circuit between the electrodes.

The state of the art is illustrated in French published patent specification No. 2 204 520. Practical fabrication difficulties are also explained in another French published patent specification No. 2 339 169 in which proposals are made to use a hydrophilic material comprising one or more monomolecular films.

Preferred implementations of the present invention provide a method of fabricating a short response time thin film sensor in which the dielectric is made more easily than before, and may even be made on an irregular base. In addition, such implementations of the invention do not suffer from a high reject rate.

As a result of such simpler and easier fabrication, sensors can be made more cheaply than before.

SUMMARY OF THE INVENTION

The present invention provides a method in which the improvement over prior methods lies in the fact that at least two different films of polymer are deposited on a base substrate which supports a conductive film constituting a first electrode of the sensor, the two polymer films being mutually compatible but including specific different solvents, the first film being chosen for ease of spreading in a regular film over a rough surface and for its capacity to adhere to said surface, and the second film being chosen for its dielectric properties as a function of humidity.

The use of two successive films of polymer in accordance with the invention has a first important consequence.

In accordance with a preferred feature of the invention, the substrate is made from conventional printed circuit card material having at least one face with a film of copper thereon which can readily be given any desired shape to constitute one of the electrodes of the sensor.

In a preferred implementation of the method according to the invention first and second electrodes separated by a gap are formed on the printed circuit card medium serving as the substrate, the successive films of polymer are then deposited over the electrodes, the films of polymer are removed from various points over the second electrode, and a film of metal is then deposited over the top film of polymer, thus coming into contact with the second electrode at the points thereof from which the polymer films had been removed.

A capacitor component is thus obtained having one plate constituted by the said first electrode formed on the printed circuit medium, and having its other plate constituted by the deposited film of metal which comes into contact with the said second electrode on the printed circuit medium, which second electrode is separated from the first electrode by the said gap. There is thus no problem in connecting the capacitor component to an electrical circuit since connections are easily made to tracks on a printed circuit card. The copper film may be relatively thick, e.g. 5 to 20 microns.

The invention also makes it possible to obtain an additional advantage.

The first and second electrodes can be given any desired shape by etching away the unwanted portions of the copper film on the substrate. In particular, the first electrode, i.e. the electrode which does not make contact with the top film of metal, may be given a zigzag shape typical of a printed circuit resistance, said zig-zag extending between two connection tabs. This, the first electrode, which is one of the plates of a capacitor, also constitutes a resistive component between two connection points with a resistance value that changes as a function of temperature. This thus provides a combined temperature and humidity sensor on a single support. The sensor is cheap and easy to fabricate and it is possible to achieve an extremely low reject rate.

In a first variant, the temperature sensor and the humidity sensor are made on the same face of the substrate. In a second variant, they are made on opposite faces.

BRIEF DESCRIPTION OF THE DRAWINGS

Embodiments of the invention are described by way of example with reference to the accompanying drawings, in which.

MORE DETAILED DESCRIPTION

Figure 1:
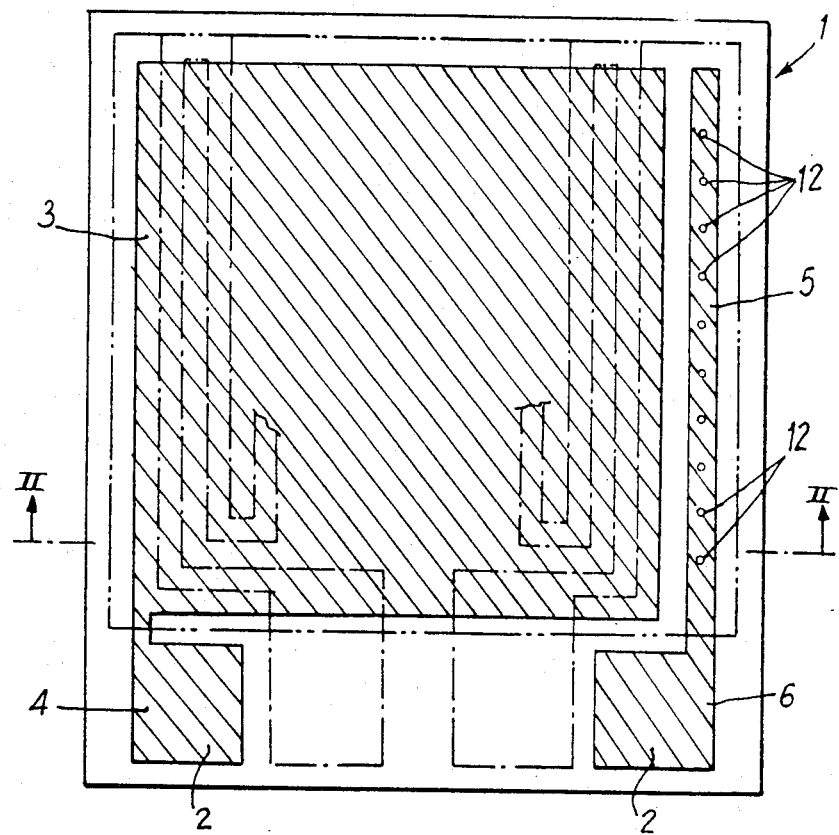
FIG. 1 is a plan view of a humidity sensor in accordance with the invention, together with an optional temperature sensor on the opposite face of the substrate and shown by dot-dashed lines.
Figure 2:
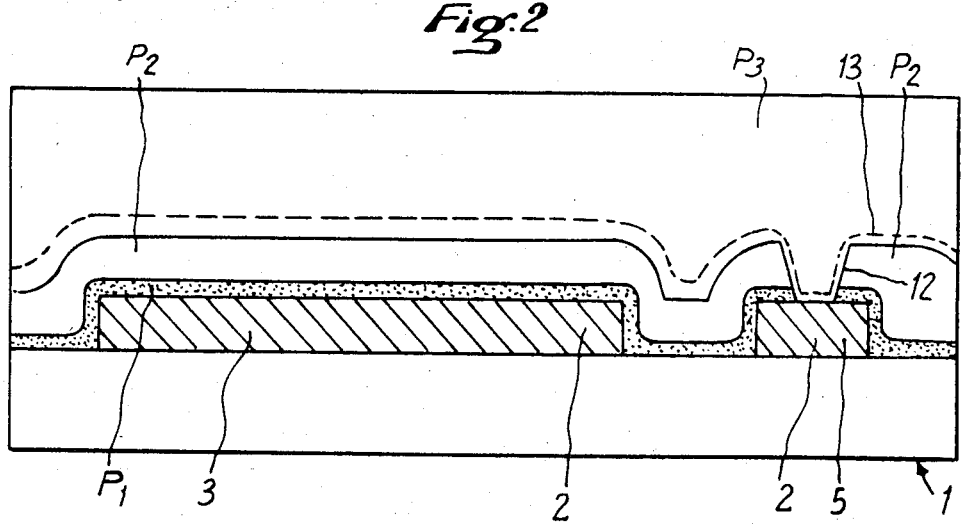
FIG. 2 is a highly enlarged section on a line II—II through the humidity sensor shown in FIG. 1.

A substrate 1 is made from commercially available material for making printed circuit cards, having a film of copper 2 on one face (or alternatively, in a variant, on both main faces). A suitable material is sold under the name KAPTON 127 M and has a film of copper with is 9 microns thick. Glass-epoxy sheets covered in a film of nickel or nickel-chrome, or aluminum, etc. would also be suitable.

The substrate is preferably subjected to a stabilizing heat treatment cycle by being repetitively cycled from +20° C. to +130° and back again over a period of 24 hours.

The substrate is then chemically etched in conventional manner for printed circuit card manufacture to form thereon a first electrode 3 of relatively large size and having a connection tab 4, and a second electrode 5 of relatively small size and having a connection tab 6 which is kept apart from the tab 4. The second electrode 5 is preferably in the form of a narrow strip running along one side of the first electrode 3.

A first film P1 of polymer is then deposited on the substrate over its surface on which the electrodes 3 and 5 are formed. The connection tabs 4 and 6 are left clear of the polymer which is deposited in the rectangular region marked by a double-dot-dashed line in FIG. 1. The first film of polymer is hydrophobic, e.g. a 3% solution of polyurethane, and it is 0.3 microns thick. This film spreads easily without requiring special precautions, for example a brush may be used. The polymer is chosen to have high wetting power so as to make it spread easily and so as to make it adhere well to the substrate, to the electrodes and to a second film of polymer.

This first film P1 of polymer acts as a barrier: it keeps the capacitor plates apart and it smoothes out surface irregularities caused by the etching process.

A second film P2 of polymer is then deposited on the first. The second polymer constitutes the sensitive component of the hygrometric sensor. It is chosen for its electrical properties in relation to humidity. It may be a few tenths of a micron to several tens of microns thick. For example, a 10% solution of cellulose acetate butyrate ester may be used. The solvent or the mixture of solvents in the film P2 must be chosen in such a manner as to have practically no effect on the first film P1.

The thickness of the second film P2 must be as regular as possible over the first electrode 3. This thickness may be 1.4 microns, for example.

Figure 5:
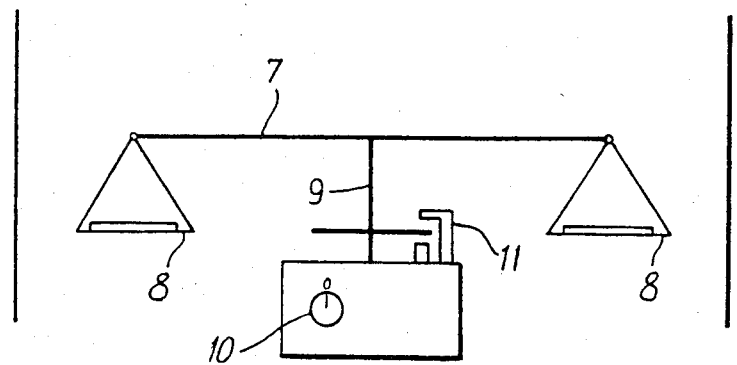
FIGS. 5, 6 and 7 are diagrammatic views showing three stages in the performance of the method of the invention.
Figure 6:
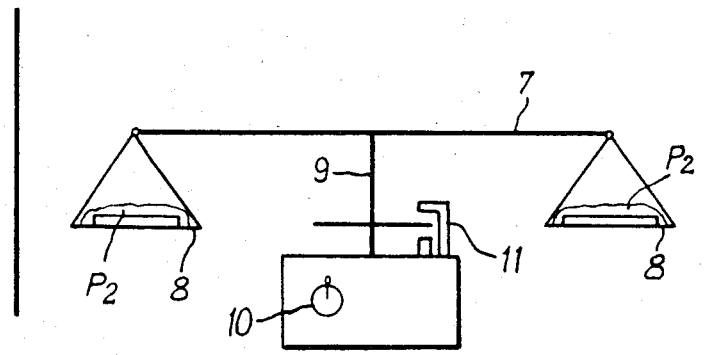
Figure 7:
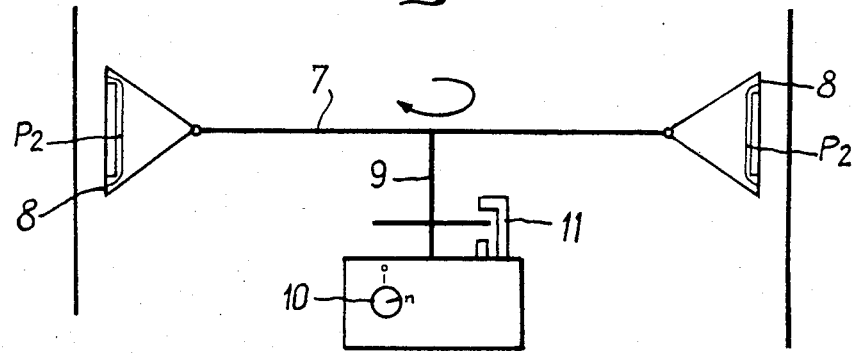

In order to obtain regular thickness, a smooth surface, and good chances of success in a reproducible manner, vertical centrifuge processing is preferably employed as shown in FIGS. 5 to 7.

A rotor having a plurality of rotary arms 9 (e.g. four arms) has a horizontal pan 8 suspended from the free end of each arm 7 in such a manner as to be capable of taking up a vertical position when the supporting arms 7 are spun about a central vertical shaft 9. The rotor has a variable speed control and an opto-electronic revolution counter 11. An etched substrate covered with the first polymer film P1 is placed in each pan 8. The second film P2 is spread thereover as well as possible by hand and then the rotor is set into motion so that the pans 8 are kept substantially vertical (FIG. 7) until the film P2 has dried. Centrifugal force is exerted evenly over the surface of the pans 8 and causes the film P2 to become uniform and to remain uniform. Gravity tends to cause a downwards flow, but the resulting difference in thickness is very small and its effects are hard to measure. The relative effect of gravity is naturally reduced by increasing the centrifugal force due to rotation.

After this operation, the films P1 and P2 are removed from several points over the second electrode 5 to bare the surface thereof. The polymer films are thermally or mechanically perforated at a plurality of points 12 along the electrode 5 (see FIG. 1).

A porous film of metal 13 having a thickness of 150 to 400 Å is then deposited by vacuum metallization or by cathode sputtering. Suitable metals include gold, nickel, nickel-chrome, . . . , or any other metal or alloy which is slow to oxidize or corrode. This is the only expensive operation in the method of the present invention.

The metal film 13 is kept separate from the electrode film 3 by the dielectric constituted by the films P1 and P2. It is directly connected to the electrode 5 at the points 12.

This provides a very cheap hygrometric sensor which can easily be connected to an electric circuit by means of the connection tabs 4 and 6. Such a sensor has a time constant of about one second. This constant depends on the thickness of the films P1 and P2. Its useful life is short (a few months) because the porous metal film 13 which is thin and fragile is not protected.

This can be cured by depositing an additional film P3 over the metal film 13 using a 10% solution of polyurethane similar to that used for the second film P2 except that it must use a solvent mixture with is chosen to have no effect on the film P2.

The additional film P3 provides mechanical protection which facilitates handling of the protected sensor. It may be a few microns to a few tens of microns thick. It is porous to humidity. It serves to lengthen the service life of the sensor to several years, but also increases its response time to 1 or 2 minutes.

Figure 3:
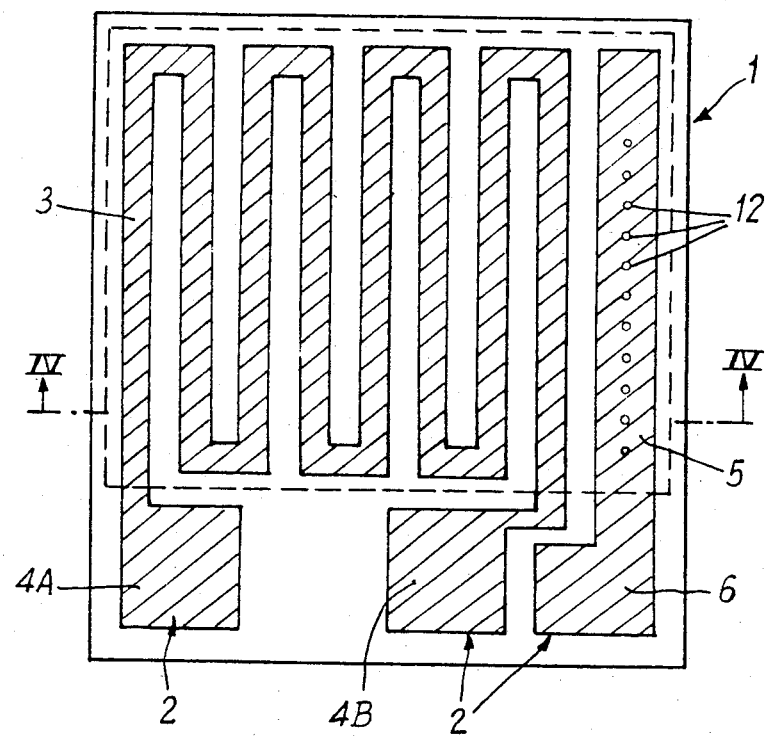
FIG. 3 is a plan view of a combined temperature and humidity sensor fabricated in accordance with the invention and on a single face of the substrate.
Figure 4:
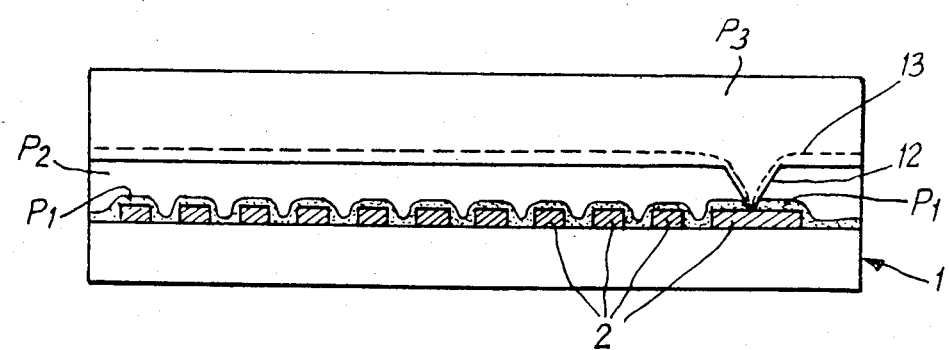
FIG. 4 is a highly enlarged section on a line IV—IV through the combined sensor shown in FIG. 3.

The geometrical configuration of the first electrode 3 is not restricted by the invention. It may thus be given any shape which may be desired for other considerations. In particular as shown in FIGS. 3 and 4, the first electrode 3 may be given the typical shape of a printed circuit resistance, i.e. it may be a sinuous narrow strip following a plurality of U-shapes between a first connection tab 4A and a second connection tab 4B. There is thus an electrical resistance between these two tabs which varies as a function of temperature, thereby enabling temperature to be measured. A two-function sensor is thus obtained, with a hygrometer between the tab 6 and the tabs 4A and 4B taken together, and with a thermometer between the tabs 4A and 4B taken separately. The films P1, P2 13, and optionally P3 are deposited thereon in the same manner as explained above.

A particular two-function sensor as illustrated in FIGS. 3 and 4 is constituted by: a first film P1 which 0.3 microns thick and made from a 3% solution of polyurethane; a second film P2 which is 1.4 microns thick and made from a 10% solution of cellulose acetate butyrate ester; a porous metal film 13 which is 250 Å thick and made of gold; and the optional third film P3 which is made of a 10% solution of polymethane. It has the following characteristics:

Temperature sensor nominal resistance $R_O = 30\Omega \pm 10\%$;
sensitivity coefficient $A = 4.21.10^{-3}/°$ C. $\pm 0.005$
where $R(T) = R_O(1 + AT)$;
linearity over an 80° C. range $\pm 0.2°$ C.;
drift: not detectable after three months operation in the range +30° C. to −65° C.

Hygrometric sensor nominal capacitance $C_O = 500$ pF $\pm 10\%$;
sensitivity coefficient $K = 2.5 \ 10^{-1}/°$ C. $\pm 0.05$,
where $1/C(U) = 1/C_O(1 + KU)$;
linearity between 10% and 97% $\pm 1.4\%$;

hysteresis: not distinguishable (included in the figure for linearity);

temperature influence <0.1%/° C.;

drift: not detectable after three months outdoor operation;

time constant at 20° C.:
without a film P3<1.7 s at 63% humidity
with the film P3<60 s at 63% humidity.

It is not essential to use one of the electrodes of the capacitor to make a two-function sensor. Starting from a double sided substrate (i.e. having a film of metal on both large faces), a hygrometric sensor can be made on one face as shown by solid lines in FIG. 1, while a temperature sensor can be made on the opposite face as shown by dot-dashed lines in FIG. 1.

Printed circuit material is sold commercially in sheets which are much larger than required for a sensor. A single sheet may therefore be etched in a single operation, on one or both faces, to produce the electrodes for a plurality of one or two function sensors which may then be simultaneously covered with the films P1, P2, 13 and optionally P3 before being cut up into individual sensors. The film P3 is useful in this context. It protects the extremely thin metal film 13 and it fills the holes 12 so that the substrate can be cut up without having to take special precautions. In addition, since the film P3 completely covers the thin film of metal 13 and protects it from the environment, it is not essential for this film to be made of an expensive stainless metal such as gold; aluminum is adequate.

Finally, the method of the invention eliminates difficult and expensive operations, makes it possible to fabricate a plurality of two-function sensors simultaneously, and eliminates the risk of damage when connections are soldered to the sensors. As a result, a sensor fabricated in accordance with the invention is about five times cheaper than previously available sensors.

In the above description, various polymers suitable for use in the invention are specified: numerous other materials are commercially available either in dry form or in solution which could be used. According to the invention, the important point is to use specific solvents selected so that each film remains intact when the next film is deposited thereon.

We claim:

1. A method of fabricating a thin film sensor comprising a support, a first film of metal constituting a first capacitor plate, a polymer-based dielectric film, and a second film of metal constituting a second capacitor plate, wherein:

the dielectric film is deposited as at least a first film of polymer which is hydrophobic and a second film of polymer which is sensitive to humidity, these polymer films being made from solutions based on different specific solvents, with the first polymer film being suitable for spreading well and ensuring good adherence, and with the second polymer film being chosen for its dielectric qualities;

the support being made from a printed circuit type of substrate having a conductive film on at least one face;

first and second distinct electrodes with respective connection tabs being made in said conductive film by etching;

a first film of hydrophobic polymer being deposited thereon;

a second film of humidity sensitive polymer being deposited on the first film of polymer;

both films of polymer being removed at a plurality of points over the second electrode, to bare the second electrode;

a porous film of metal being deposited on the assembly, thereby making electrical contact with the second electrode via said bared points and thus constituting a second capacitor plate, suitable for co-operating via the dielectric constituted by the films of polymer with the first electrode constituting the first capacitor plate; and the said tabs being reserved as terminals for connecting the sensor to an electrical circuit.

2. A method according to claim 1, wherein the first electrode is made in the shape of a printed circuit resistor extending between two separate tabs for connection to an electrical circuit, thereby obtaining a two-function sensor comprising a hygrometer for connection between the second electrode tab and the tabs of the first electrode taken together, and a thermometer for connection between the tabs of the first electrode.

3. A method according to claim 1, wherein the substrate used has a thin conductive film on both of its opposite faces, and wherein a hygrometer according to claim 1 is made on one of said faces and an independent printed circuit resistance is made on the other face to constitute a temperature sensor.

4. A method according to claim 1, wherein a final film of hydrophilic polymer is deposited over the film of metal to a thickness of a few microns to several tens of microns using a solution whose solvent is different from the second film solvent.

5. A method according to claim 4, wherein the final film uses a 10% solution of polyurethane.

6. A thin film sensor comprising a support, a first film of metal constituting a first capacitor plate, a polymer based dielectric, and a second film of metal constituting a second capacitor plate, the sensor including the improvements wherein the support is a printed circuit type of substrate having a conductive film on at least one face, which film is shaped to constitute a first electrode connected to a first connection tab and a second electrode connected to a second connection tab, the dielectric comprises at least one film of polymer spread over the two electrodes, and the second film of metal is porous, is deposited on the polymer film, and makes electrical contact with the second electrode at bare points thereon where the polymer film is absent.

7. A sensor according to claim 6, wherein the first electrode has the shape of a printed circuit resistance extending between two separate connection tabs.

8. A sensor according to claim 6, wherein the polymer film comprises at least a first hydrophobic film deposited on the electrodes and a second hydrophilic film deposited on the first film.

9. A thin film sensor wherein the support is a substrate of the printed circuit type having a conductive film on both large faces, one of the faces constituting a sensor according to claim 6 and the other face having a printed circuit type resistance extending between two connection tabs.

10. A sensor according to claim 6 including a final film of hydrophilic polymer having a thickness of a few microns to several tens of microns.

11. A method for fabricating a thin film sensor, comprising the steps of:

depositing a first film of hydrophobic polymer on a printed circuit-type substrate having a conductive film on at least one face;

depositing on said first film a second film of polymer sensitive to humidity;

said polymer films being made from solutions based on different specific solvents, said first polymer film being suitable for spreading well and ensuring good adherence with said substrate and said second polymer film, said second polymer film being chosen for its dielectric quality; and depositing a porous film of metal on said second film.

12. A method according to claim 11, wherein the first polymer film is given a thickness of a few tenths of a micron.

13. A method according to claim 12, wherein the second film of polymer is spread by centrifuging with the substrate in a vertical position.

14. A method according to claim 11, wherein the second polymer film is given a thickness of one to several microns.

* * * * *